(12) United States Patent
Baird et al.

(10) Patent No.: US 10,736,587 B2
(45) Date of Patent: Aug. 11, 2020

(54) RADIATION SCATTER PROTECTION SYSTEM

(71) Applicants: David A. Baird, Rome, OH (US); Thomas P. Hink, Euclid, OH (US); Denio A. Leone, Rocky River, OH (US)

(72) Inventors: David A. Baird, Rome, OH (US); Thomas P. Hink, Euclid, OH (US); Denio A. Leone, Rocky River, OH (US)

( * ) Notice: Subject to any disclaimer, the term of this patent is extended or adjusted under 35 U.S.C. 154(b) by 0 days.

(21) Appl. No.: 16/414,375

(22) Filed: May 16, 2019

(65) Prior Publication Data

US 2019/0350542 A1    Nov. 21, 2019

Related U.S. Application Data

(60) Provisional application No. 62/672,688, filed on May 17, 2018.

(51) Int. Cl.
| | |
|---|---|
| *A61B 6/10* | (2006.01) |
| *A61B 6/04* | (2006.01) |
| *G21F 1/12* | (2006.01) |
| *G21F 3/00* | (2006.01) |

(52) U.S. Cl.
CPC ............ *A61B 6/107* (2013.01); *A61B 6/0407* (2013.01); *G21F 1/125* (2013.01); *G21F 3/00* (2013.01)

(58) Field of Classification Search
CPC ....... A61B 6/107; A61B 6/0407; G21F 1/125; G21F 3/00
See application file for complete search history.

(56) References Cited

U.S. PATENT DOCUMENTS

2017/0119324 A1*   5/2017   Wilson ...................... G21F 1/12

\* cited by examiner

*Primary Examiner* — Nicole M Ippolito
*Assistant Examiner* — Hanway Chang
(74) *Attorney, Agent, or Firm* — Daniel M. Cohn; Howard M. Cohn (57) ABSTRACT

A radiation scatter protection system designed to attach to an X-ray table to limit exposure to radiation for both medical staff and patient. The radiation scatter protection system includes an arm board adapted to be disposed around an arm of the patient; an arm board shielding including one large sheet of shielding extending downward from the X-ray table and a plurality of additional sheets of shielding, removably mounted to the arm board; a sand bag shield including a plurality of sheets of top shielding and a plurality of sheets of bottom shielding which connect to an elongated, cylindrical sandbag; a side curtain shield hanging from the X-ray table; and a throw shield.

20 Claims, 8 Drawing Sheets

RADIATION SCATTER PROTECTION SYSTEM

CROSS REFERENCE TO RELATED APPLICATIONS

This application claims the benefit of U.S. Provisional Patent Application No. 62/672,688 filed on May 17, 2018, which is incorporated in its entirety by reference herein.

TECHNICAL FIELD OF THE INVENTION

The present invention relates to a radiation scatter protection system, and more particularly to protection system designed to limit exposure to radiation for both medical staff and patients.

BACKGROUND OF THE INVENTION

In the medical field, personnel are often required to work in close proximity to patients undergoing imaging procedures involving x-rays, commonly referred to as fluoroscopy. The hazard to the worker arises from x-rays scattered by the patient's body toward the worker. Although such scattered radiation has a lower energy level than the direct x-ray beam, it does maintain its ionizing potential. Exposure to this scattered radiation has the potential to produce a significant radiation hazard over the working lifetime of the worker. For this reason, workers traditionally wear a radiation shielding garment that places a protective barrier between the scattering tissues of the patient and the body of the worker.

Traditionally such garments are made from a flexible rubber or polymer material within which is embedded powdered lead, a good absorber of x-rays. Unfortunately, lead garments are heavy and can cause significant injury to the wearer with daily use over a working lifetime. There has thus begun a search for lighter weight materials which can provide equivalent protection under the conditions of this job.

An underlying principle of such reduced weight garments is that for a large portion of the x-ray energy levels commonly used in medical procedures, certain elements, provide greater attenuation per unit weight than lead. Until now, most workers have assumed that the testing of the effectiveness of such elements other than lead requires meeting the requirements of shielding from the effects of the direct x-ray beam from the x-ray source.

It is now realized, however, that the danger to the worker is primarily caused by radiation reflected from the patient's body, so-called "scattered radiation". An additional problem, however, arises from the fact that many of these lower atomic number heavy metals reradiate the x-rays they absorb, albeit at lower energy levels. This can lead to a problem where the exposure to the wearer is greater than that evident from the attenuation tests.

SUMMARY OF THE INVENTION

According to an embodiment of the present invention, there is disclosed a radiation scatter protection system designed to attach to an X-ray table to limit exposure to radiation for both medical staff and patient. The radiation scatter protection system includes an arm board adapted to be disposed around an arm of the patient; an arm board shielding including one large sheet of shielding extending downward from the X-ray table and a plurality of additional sheets of shielding, removably mounted to the arm board; a sand bag shield including a plurality of sheets of top shielding and a plurality of sheets of bottom shielding which connect to an elongated, cylindrical sandbag; a side curtain shield hanging from the X-ray table; and a throw shield.

According to an embodiment of the present invention, there is disclosed a method for attaching a radiation scatter protection system to an X-ray table to limit exposure to radiation for both medical staff and patient. The method includes disposing an arm board around an arm of the patient; removably mounting an arm board shielding including one large sheet of shielding and a plurality of additional sheets of shielding to the arm board; placing atop the patient a sand bag shield including a plurality of sheets of top shielding and a plurality of sheets of bottom shielding which connect to an elongated, cylindrical sandbag; hanging a side curtain shield from the X-ray table; and placing a throw shield atop the patient.

BRIEF DESCRIPTION OF THE DRAWINGS

The structure, operation, and advantages of the present invention will become further apparent upon consideration of the following description taken in conjunction with the accompanying figures (FIGS.). The figures are intended to be illustrative, not limiting. Certain elements in some of the figures may be omitted, or illustrated not-to-scale, for illustrative clarity. The cross-sectional views may be in the form of "slices", or "near-sighted" cross-sectional views, omitting certain background lines which would otherwise be visible in a "true" cross-sectional view, for illustrative clarity.

In the drawings accompanying the description that follows, both reference numerals and legends (labels, text descriptions) may be used to identify elements. If legends are provided, they are intended merely as an aid to the reader, and should not in any way be interpreted as limiting.

DETAILED DESCRIPTION OF THE PREFERRED EMBODIMENTS

In the description that follows, numerous details are set forth in order to provide a thorough understanding of the present invention. It will be appreciated by those skilled in the art that variations of these specific details are possible while still achieving the results of the present invention. Well-known processing steps are generally not described in detail in order to avoid unnecessarily obfuscating the description of the present invention.

In the description that follows, exemplary dimensions may be presented for an illustrative embodiment of the invention. The dimensions should not be interpreted as limiting. They are included to provide a sense of proportion. Generally speaking, it is the relationship between various elements, where they are located, their contrasting compositions, and sometimes their relative sizes that is of significance.

In the drawings accompanying the description that follows, often both reference numerals and legends (labels, text descriptions) will be used to identify elements. If legends are provided, they are intended merely as an aid to the reader, and should not in any way be interpreted as limiting.

Physicians and allied clinical personnel, collectively referred to as medical staff, are commonly involved in medical procedures involving patients in which fluoroscopic and other types of radiation systems (such as computer tomography, or CT systems) are used for purposes of diagnostic detection or guidance procedures. These radiation systems allow the medical staff to peer into the body systems of a patient with minimal invasiveness. The images generated may be in the form of a single image, or a video feed, both of which may be live. For example, the anatomy of a patient may be illuminated using x-rays so that the medical staff can carry out medical procedures using a fluoroscopic viewing screen. In one case, x-ray fluoroscopy may be used to indirectly guide the placement of a surgical device within the patient during a surgical procedure.

When working with a patient on an x-ray table, doctors and other medical personnel can be exposed to primary radiation that emanates directly from the source and/or exposed to secondary radiation that is scattered by an object such as the x-ray detector, the x-ray table, and even the patient. Traditionally, there have been apparatuses and methods for protecting and shielding against radiation in x-ray laboratories. Though there are numerous shapes and designs for protective shields, and although they may be constructed of various materials, they do not sufficiently protect against radiation exposure, and thus medical personnel must still wear heavy and encumbering leaded protective clothing.

The radiation scatter protection system 10 (hereafter "protection system 10") is designed to limit exposure to radiation for both medical staff and patients. It is also desirable to protect medical staff members from radiation in a way that does not interfere or limit them from conducting their medical procedures.

Figure 5:
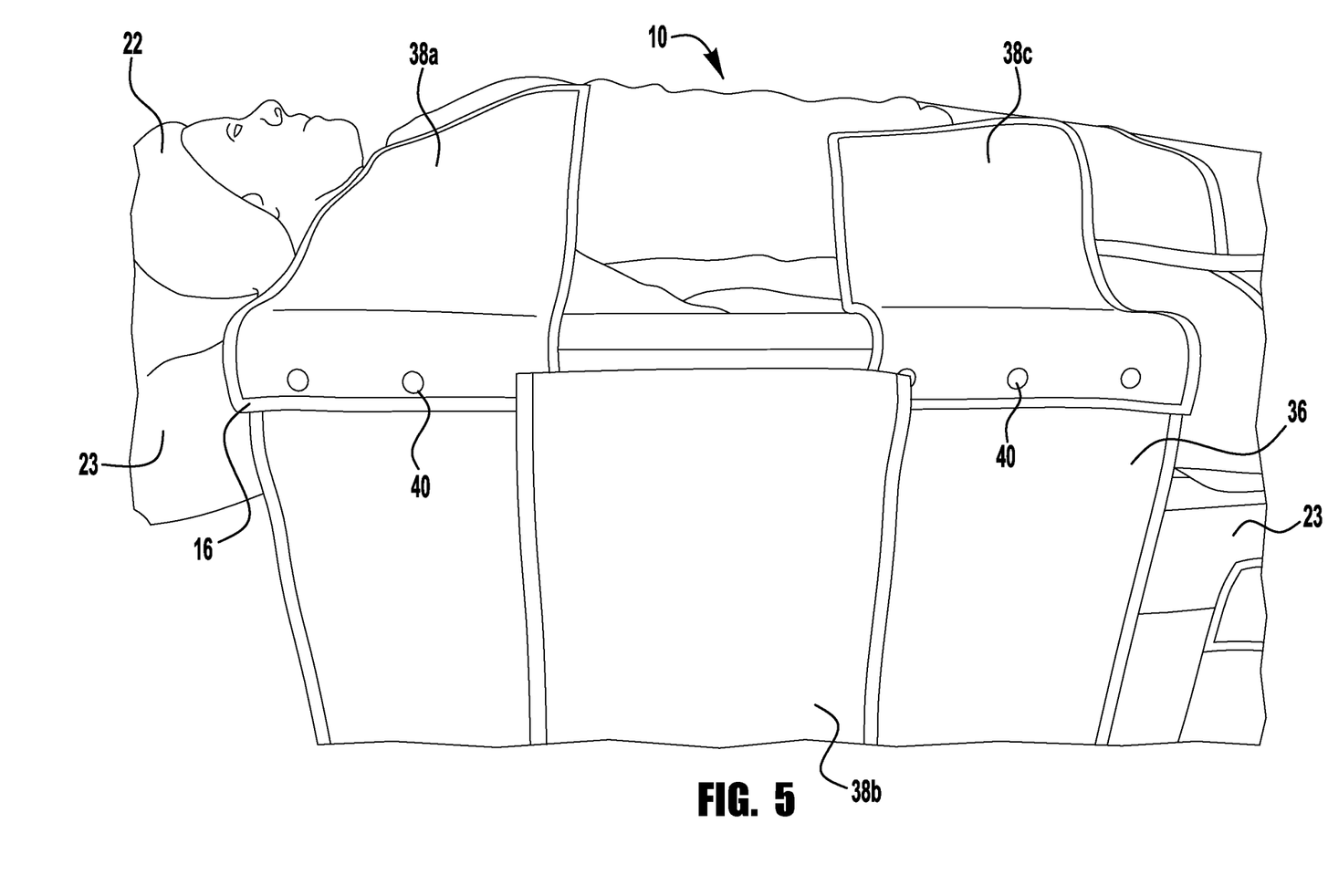
FIG. 5 is a side, three-dimensional view showing the radiation scatter protection system covering a patient lying on an X-ray table with the plastic arm board shown in FIG. 4 disposed underneath and adjacent the patient lying on an X-ray table, in accordance with the present invention.
Figure 6:
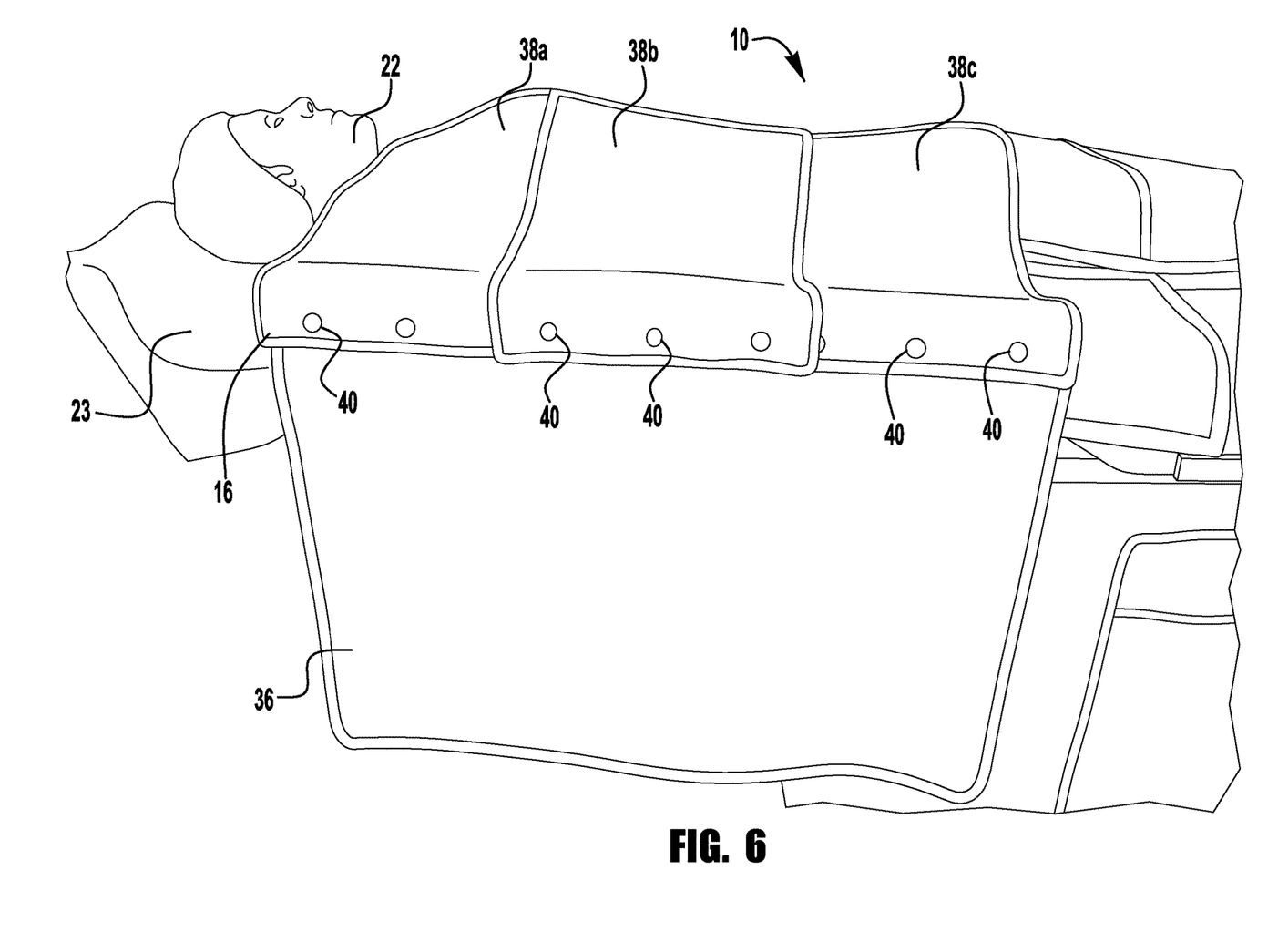
FIG. 6 is a side, three-dimensional view of the radiation scatter protection system covering a patient lying on an X-ray table, as shown in FIG. 5 with the radiation scatter protection system completely covering the patient, in accordance with the present invention.
Figure 7:
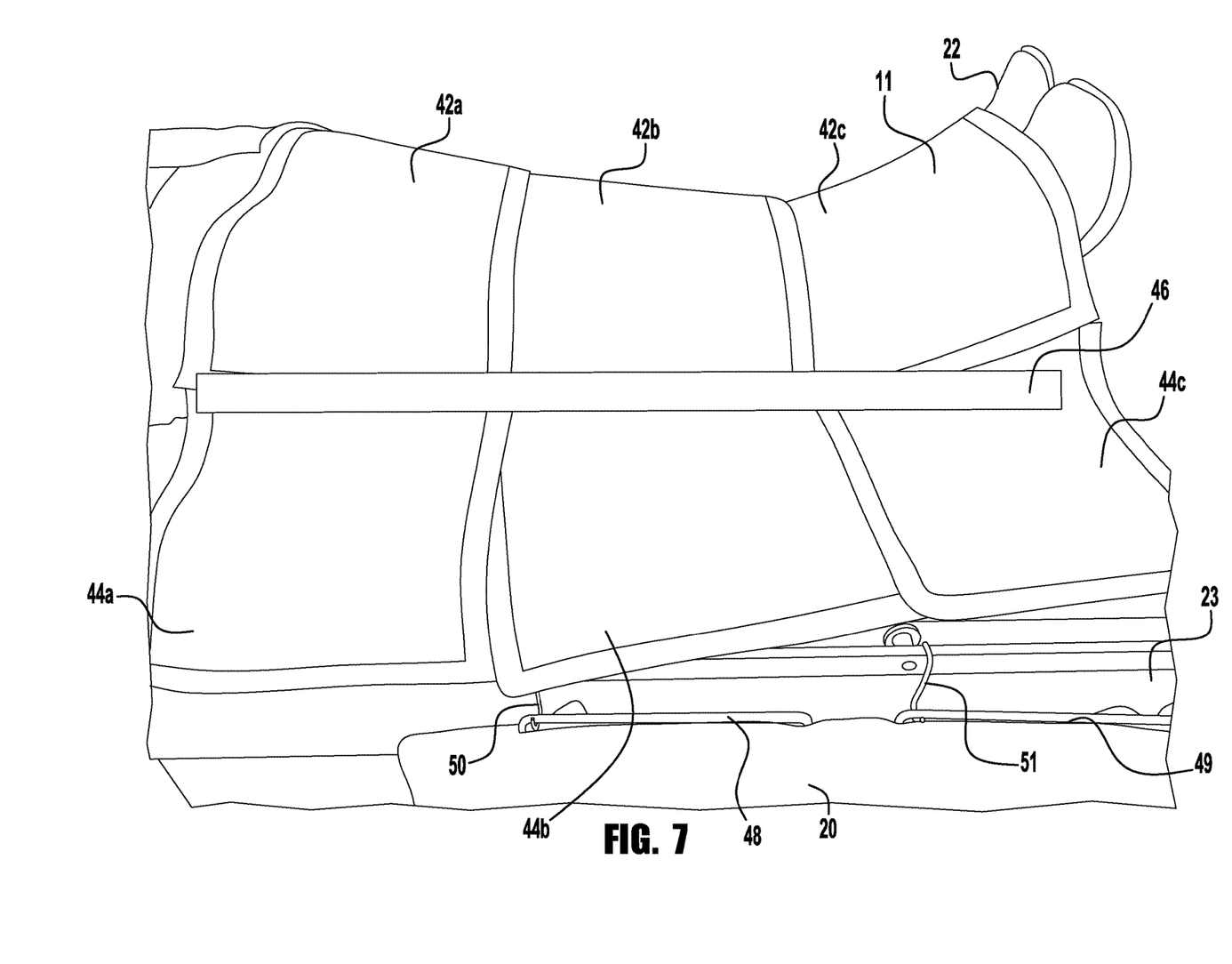
FIG. 7 is a side, three-dimensional view of a sandbag shield of the radiation scatter protection system covering the legs of a patient, in accordance with the present invention.

FIGS. 1-8 illustrate the various components that collectively form the protection system 10. In general terms, the protection system 10 includes one or more plastic arm boards 12, arm board shielding 16, a sandbag shield 18 as shown in FIG. 7, a side curtain shield 20, and a throw shield 21. The plastic arm boards and the various shields described hereinafter are designed to minimize the risk of radiation exposure to both the medical staff, and the patient 22 during a medical procedure requiring the use of X-ray. An aluminum hanger to mount on the wall may be provided to store the elements of the protection system 10.

Figure 2:
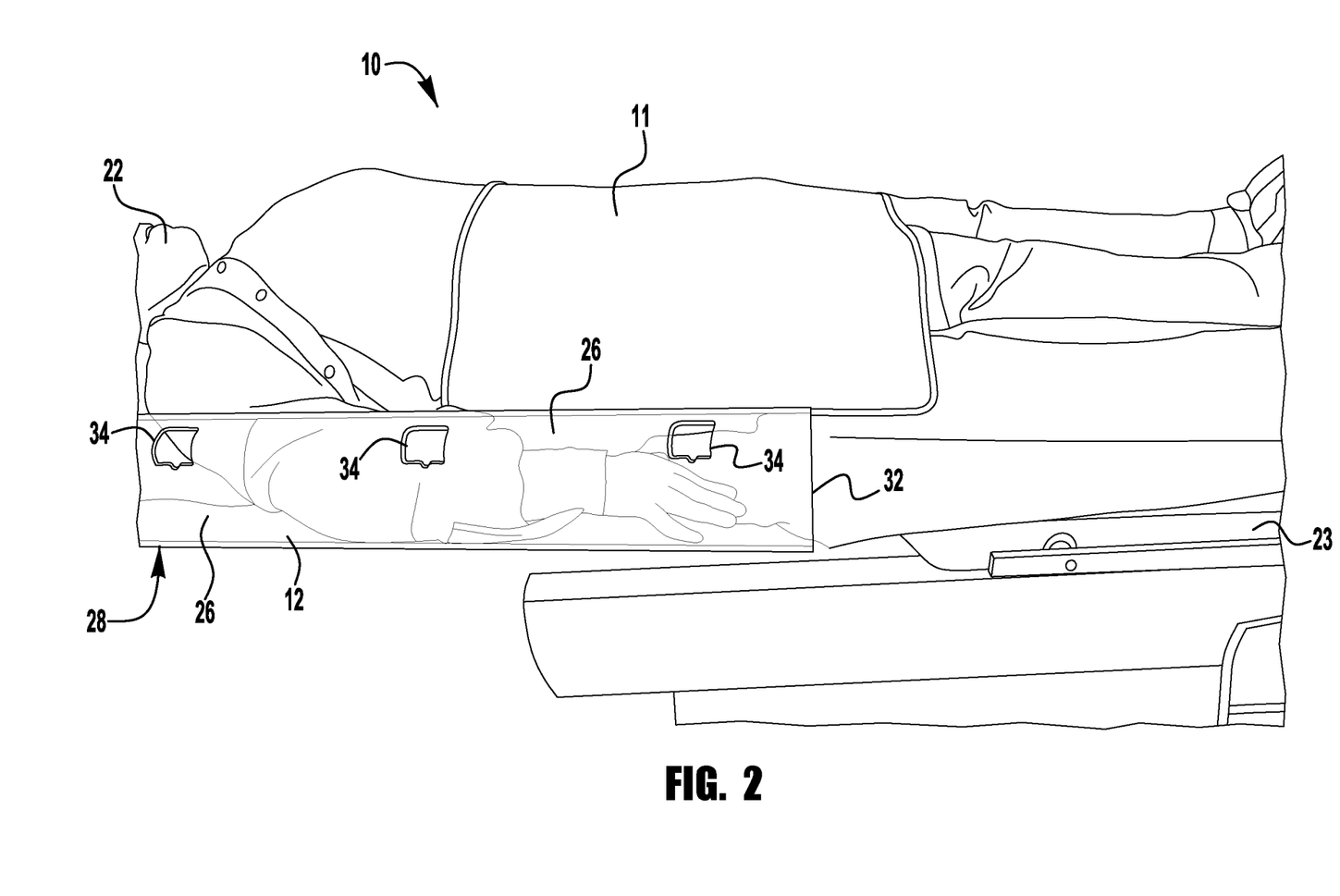
FIG. 2 is a side, three-dimensional view of a plastic arm board of the radiation scatter protection system disposed underneath and adjacent the patient lying on an X-ray table, in accordance with the present invention.
Figure 3:
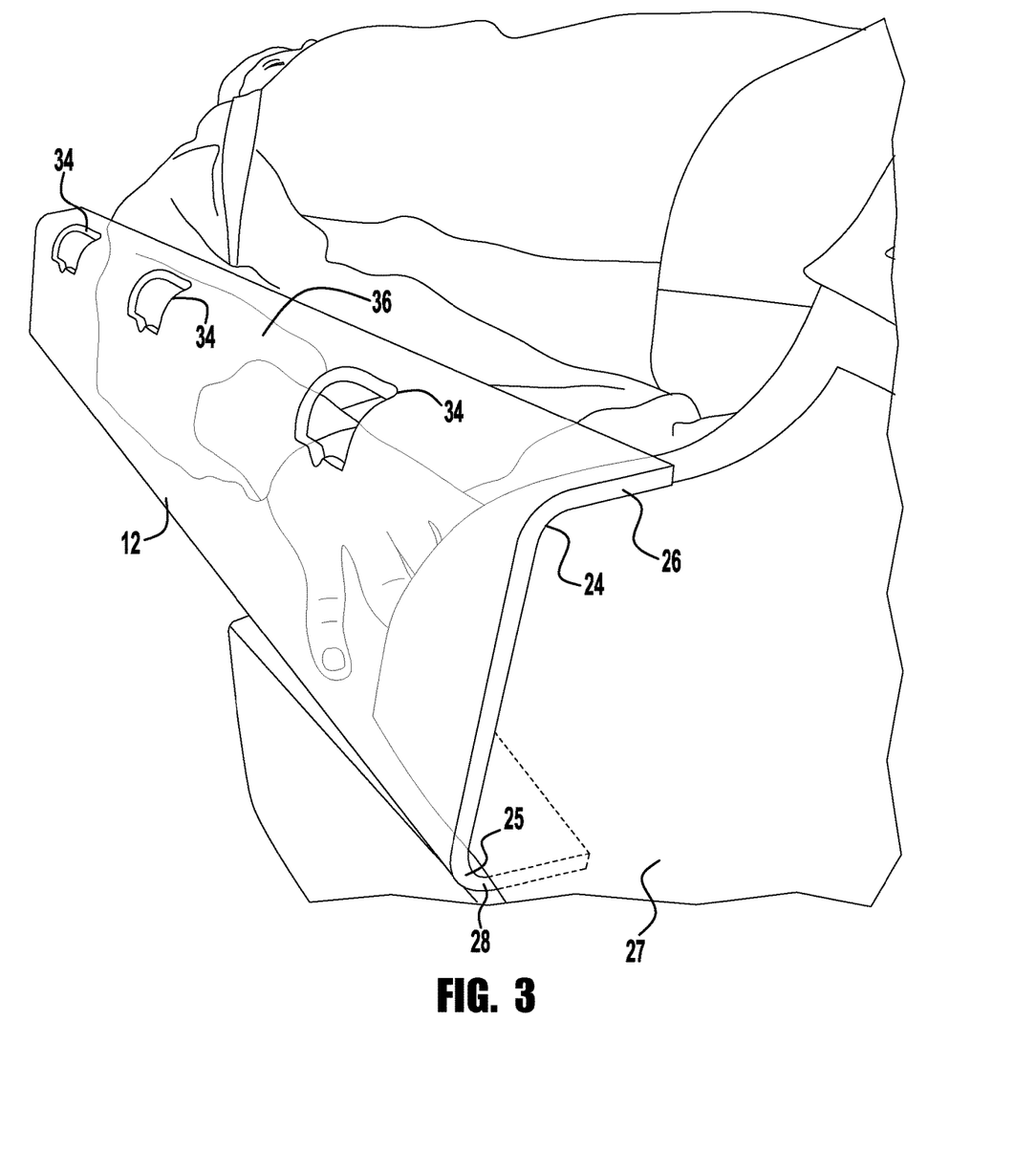
FIG. 3 is a front, three-dimensional view of the plastic arm board of the radiation scatter protection system disposed underneath and adjacent the patient lying on an X-ray table, in accordance with the present invention.
Figure 4:
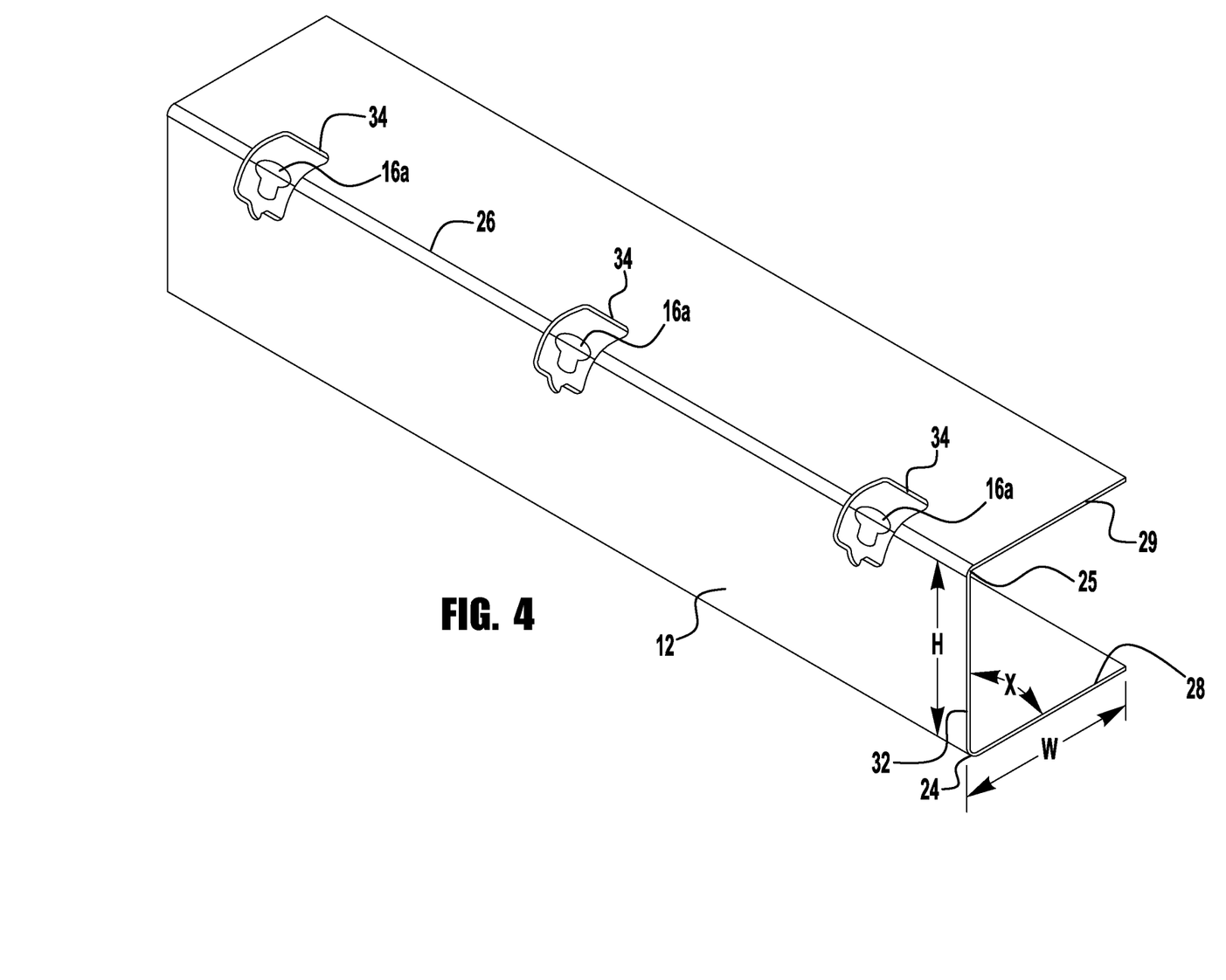
FIG. 4 is a front, three-dimensional view of the plastic arm board of the radiation scatter protection system, in accordance with the present invention.

As illustrated in FIGS. 2, 3, and 4, the plastic arm board 12 is disposed on the side of an X-ray table 23. The plastic arm board 12 is preferably manufactured from PETG (Polyethylene Terephthalate Glycol), also known as DACRON. DACRON is a condensation polymer obtained from ethylene glycol and terephthalic acid. Its properties include high tensile strength, high resistance to stretching, both wet and dry, and good resistance to degradation by chemical bleaches and to abrasion. The use of DACRON is advantageous for the present invention, since it is allows more X-rays to pass through arm board thickness than other plastics. The draw back to the use of PETG to form the plastic arm board is that the material is very har to work with and to form the radius bends 24 and 25, described herein after, is extremely difficult and tedious. Preferably, the plastic arm board 12 is formed of an approximately ¼" thick PETG plastic sheet molded into a "C" shape with first and second ¾" radius longitudinal bends 24 and 25, as seen in FIG. 4. It must be noted that the plastic arm board 12 may also be constructed with an "L" shape, with only one ¾" radius longitudinal bend. Further, it must be noted that more than one plastic arm board 12 may be utilized to offer a greater amount of protection with additional shields.

The plastic arm board 12 has exemplary overall dimensions of a width W of about 28" of a lower horizontal leg 28. A vertical leg 32 has a height h of about 11" between a first longitudinal bend 24 having a radius of about ¾" radius and a second longitudinal bend 25 having a radius of about ¾". The vertical leg 32 is preferably canted inward an angle x of about 5 and 15 degrees, and preferably about 10 degrees, off the perpendicular from the lower horizontal leg 28 to the vertical leg 32. An upper horizontal leg 29 extends inward from the vertical leg 32 and parallel to the lower horizontal leg 28.4. The first longitudinal bend 24 extends along the intersection of the upper horizontal leg and the vertical leg, and the second longitudinal bend 25 extending along the intersection of the lower horizontal leg and the vertical leg.

The arm board 12 has a plurality of notches 34 cut into the curvature 26 formed along the length of the board along the first longitudinal bend 24. The notches 34 have exemplary dimensions of 1" in wide by 1" in length, although any desired dimensions may be utilized. In use, the notches 34 disposed through the arm board 12 accept corresponding knobs protruding from the arm board shielding 16, to hold the arm board shielding in place.

As shown in FIGS. 2 and 3, with a patient 22 laying on an X-ray table 23, the bottom horizontal leg 28 of the arm board 12 is inserted under the X-ray table mattress 27, and the vertical leg 32 secures the patient's arm to the patient's side preventing the arm from swinging down and away from the table. The patient's weight holds the arm board 12 in place.

The plastic arm board 12 blocks less X-rays from the emitter disposed under the X-ray table 23 (not shown), so that the emitter in use can generate less X-rays then previously required. If the Image Intensifier disposed above the patient (not shown) senses that not enough X-ray light is coming through the patient, the Image Intensifier will cause the emitter to generate more X-rays. It's understood that more the more X-rays the patient is subjected to, the more dangerous the procedure. Being that the plastic arm board 12 is constructed of DACRON, both the technician and the patient are less at risk of radiation exposure because less X-rays are being generated, than if a protection device similar to the plastic arm board 12 is used that is not made of composite materials including DACRON.

FIGS. 5 and 6 illustrates the arm board shielding 16, which includes one larger sheet of shielding 36, extending downward from the top of table 23 to the floor. Three additional sheets of shielding 38a, 38b, and 38c overlap each other and are placed on the patient 22 and extend across the patient and above the table 23. The three sheets of shielding 38a, 38b, and 38c have one end that drapes over the arm board 12. All the shielding described herein is preferably constructed of a sheet of lead-impregnated rubber covered on both the back and the front sides with two sheets of 500 denier nylon cloth covering and sewn together around circumference of the shielding. The nylon cloth has a urethane coating on the inside surfaces against the sheet of lead-impregnated rubber for water proofing.

The shielding 36, 38a, 38b, and 38c are fastened together, such as with bolts 40 and all attach to a sheet of durable plastic sandwiched in between the bottom of the shields 38a-38c, and the top of the shield 36. The durable plastic sheet is typically approximately ¼" thick by 2" wide by 28" long and is provided to give lateral support to the shields. There are three knobs 16a, as seen in FIG. 4, bolted through the durable plastic sheet which correspond to the notches 34 of the plastic arm board 12.

The shielding 36 protects against radiation emitted from between the table 23 and the floor. The shielding 36 has exemplary dimensions of 30" wide by 24" high. The sheets of shielding 38a, 38b, and 38c drape over the patient's body, and move independently from each other to allow medical personnel to move each piece of shielding independently when necessary to access a specific area of the patient's body.

In an exemplary embodiment, the sheet of shielding 38a will be 10" wide by 16" long, the sheet of shielding 38b will be 12" wide by 16" long, and sheet of shielding 38c will be 10" wide by 16" long. The arm board shielding 16 will typically be positioned across the top of the patient's body, and hang down below the top part of the X-ray table 23.

Figure 1:
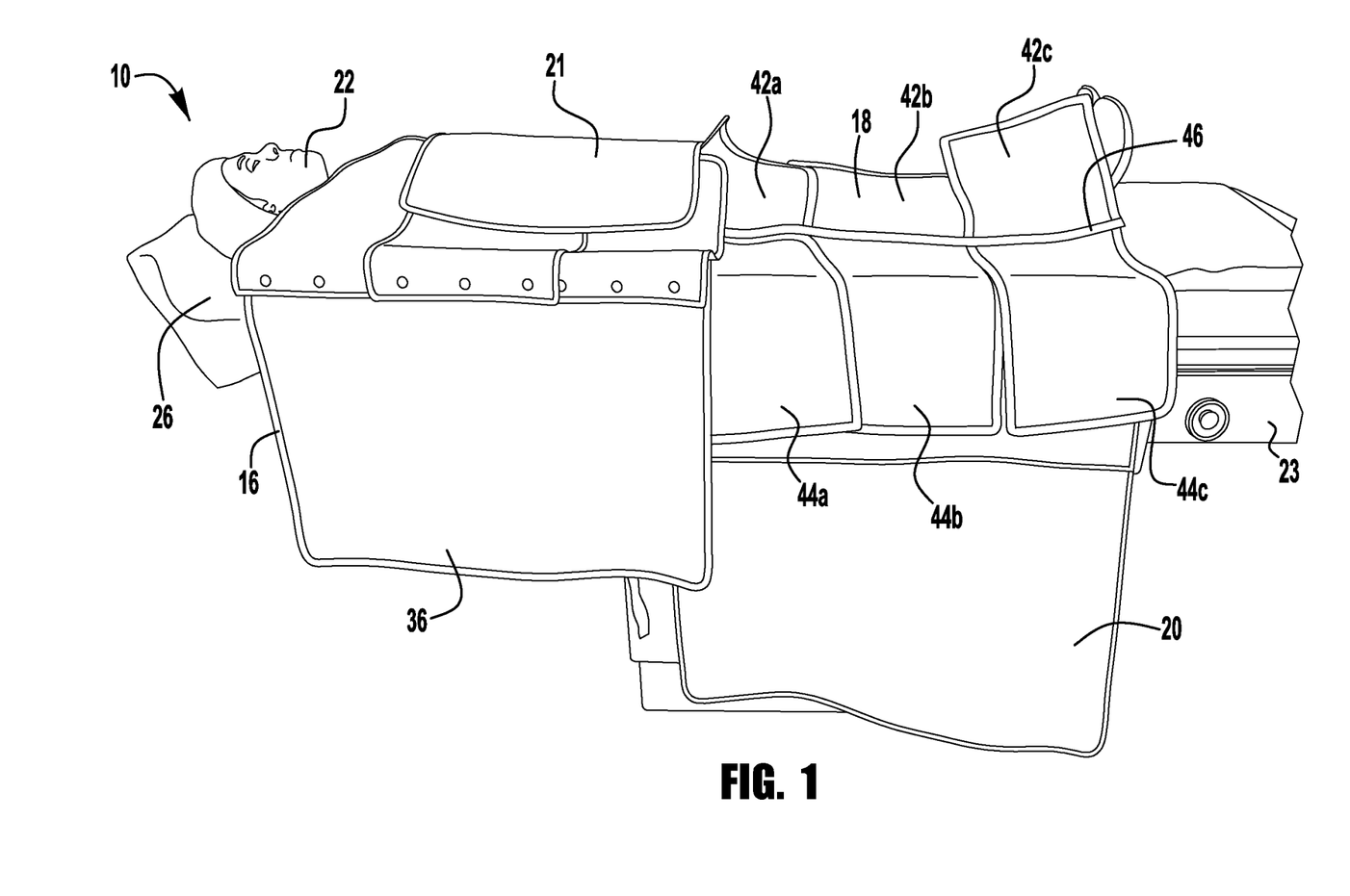
FIG. 1 is a side, three-dimensional view of the radiation scatter protection system covering a patient lying on an X-ray table, in accordance with the present invention.

The sand bag shield 18, as illustrated in FIGS. 1 and 7, includes three sheets of top shielding 42a, 42b, 42c, (42a-42c) and three sheets of bottom shielding 44a, 44b, 44c, (44a-44c) all of which connect to an elongated, cylindrical sandbag 46, to hold the shielding in place across the patient. The top sheets of shielding (42a-42c) are rectangular in shape whereby the following exemplary dimensions may be utilized, although any appropriate dimensions may be used: shield 42a will be 10" wide by 16" long, shielding 42b will be 12" wide by 16" long, and shielding 42c will be 10" wide by 16" long. The bottom sheets of shielding (44a-44c) include shielding 44a being 10" wide by 10" long, shielding 44b being 12" wide by 10" long, and shielding 44c being 10" wide by 10" long. The sandbag 46 is preferably approximately 2" in diameter and extends the width of top shielding 42a, 42b, 42c.

The shielding 42a-42c and 44a-44c move independently from each other to allow medical personnel to move each piece of shielding when needed to access a specific area of the patient's body. The top shielding 42a-42c will typically be positioned across the top of the patient's body, while the bottom shielding 44a-44c will lay across the portion of the table where technician is located and will also hang down several inches below the top of the table 23.

Figure 8:
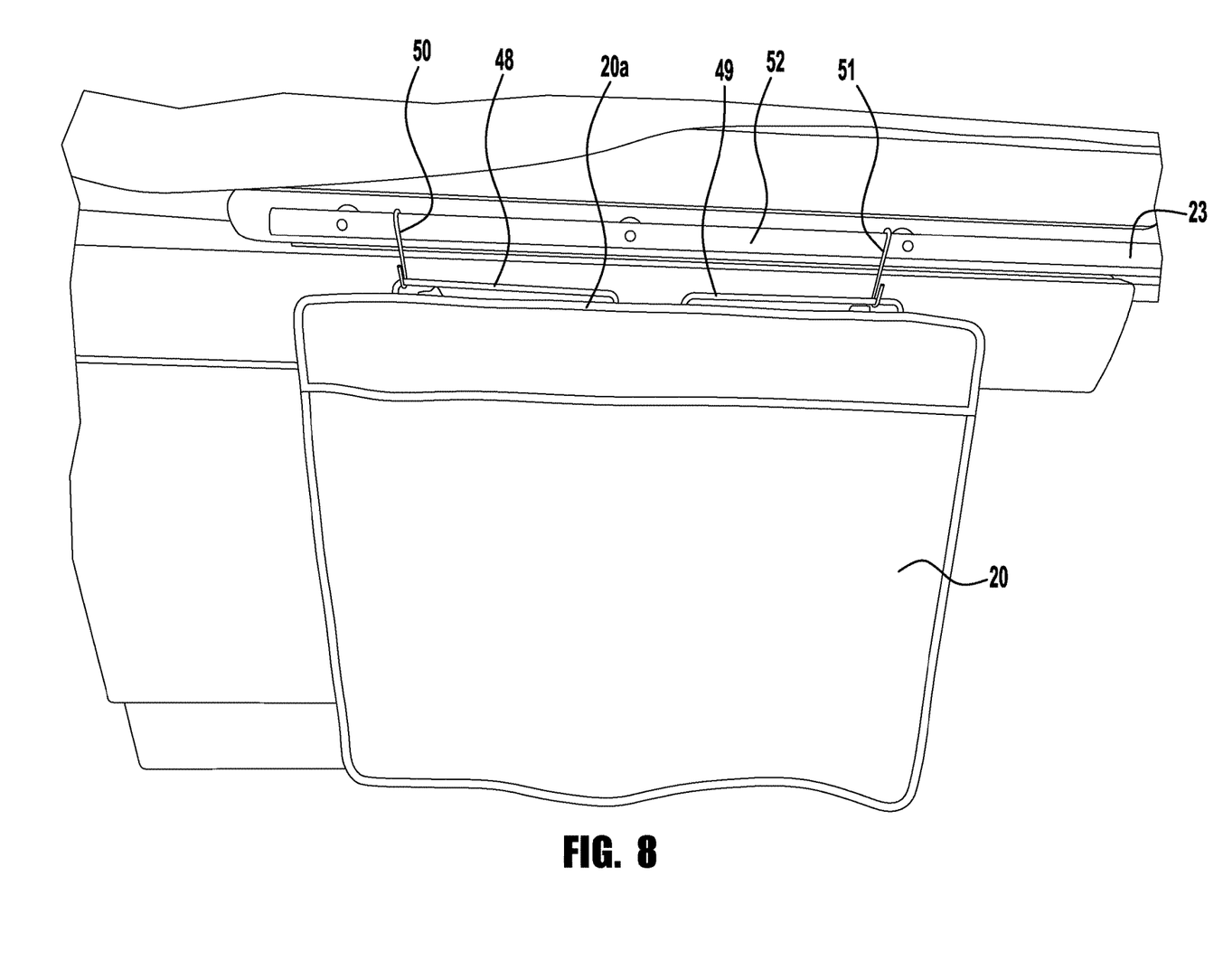
FIG. 8 is a side, three-dimensional view of the side curtain shield of the radiation scatter protection system mounted to the side of an X-ray table, in accordance with the present invention.

FIG. 8 illustrates the side curtain shield 20, which is one panel with exemplary dimensions of 30" by 28". First and second stainless steel rods 48 and 49 extend along the top 20a of the side curtain shield 20 and are secured thereto. The shield 20 hangs from the X-ray table 23 and can be secured to it with first and second "S" hooks 50 and 51, which attach to a stainless steel elongated hanger strip 52 that attached to the X-ray table 23.

A throw shield 21, as seen in FIG. 1, may be included, having exemplary dimensions of a 20" inch square. The throw shield 21 that may be used anywhere, generally to cover areas that may be exposed to radiation due to gaps in the shielding, usually caused by the relative size of the patient.

An aluminum hanger (not shown) may be included, and formed of a long solid aluminum bar. The hanger includes one or more holes, and one or more pins looped over the top edge of the aluminum bar. Typical dimensions of the hanger is ½" thick by 3" wide by 20" long. The hanger is utilized to neatly hang the various lead shielding components, described herein, so that they are not draped over other equipment in the room or hung over devices which take up further space in the procedure room.

Although the invention has been shown and described with respect to a certain preferred embodiment or embodiments, certain equivalent alterations and modifications will occur to others skilled in the art upon the reading and understanding of this specification and the annexed drawings. In particular regard to the various functions performed by the above described components (assemblies, devices, etc.) the terms (including a reference to a "means") used to describe such components are intended to correspond, unless otherwise indicated, to any component which performs the specified function of the described component (i.e., that is functionally equivalent), even though not structurally equivalent to the disclosed structure which performs the function in the herein illustrated exemplary embodiments of the invention. In addition, while a particular feature of the invention may have been disclosed with respect to only one of several embodiments, such feature may be combined with one or more features of the other embodiments as may be desired and advantageous for any given or particular application.

The invention claimed is:

1. A radiation scatter protection system designed to attach to an X-ray table to limit exposure to radiation for both medical staff and patient comprising;
    an arm board adapted to be disposed around an arm of the patient,
    an arm board shielding including one large sheet of shielding extending downward from the X-ray table and a plurality of additional sheets of shielding, removably mounted to the arm board,
    a sand bag shield including a plurality of sheets of top shielding and a plurality of sheets of bottom shielding which connect to an elongated, cylindrical sandbag;
    a side curtain shield hanging from the X-ray table, and
    a throw shield.

2. The radiation scatter protection system of claim 1, wherein the arm board is manufactured from Polyethylene Terephthalate Glycol (PETG).

3. The radiation scatter protection system of claim 2, wherein the arm board is formed of a lower horizontal leg, an upper horizontal leg, and a vertical leg which joins the bottom horizontal leg and the upper horizontal leg.

4. The radiation scatter protection system of claim 3, wherein the arm board is molded with a first longitudinal bend extending along the intersection of the upper horizontal leg and the vertical leg, and a second longitudinal bend extending along the intersection of the lower horizontal leg and the vertical leg.

5. The radiation scatter protection system of claim 4, wherein the vertical leg is canted inward at an angle x between 5 and 15 degrees between the lower horizontal leg to the vertical leg.

6. The radiation scatter protection system of claim 5, wherein the vertical leg is canted inward at an angle of about 10 degrees between the lower horizontal leg to the vertical leg.

7. The radiation scatter protection system of claim 6, wherein the arm board has a plurality of notches cut into a curvature formed along the first longitudinal bend.

8. The radiation scatter protection system of claim 2, wherein the arm board is formed of a lower horizontal leg, and a vertical leg formed of an "L" shape.

9. The radiation scatter protection system of claim 8, wherein the arm board is molded with a longitudinal bend extending along the intersection of the lower horizontal leg and the vertical leg.

10. The radiation scatter protection system of claim 9, wherein the vertical leg is canted inward at an angle x between 5 and 15 degrees between the lower horizontal leg to the vertical leg.

11. The radiation scatter protection system of claim 10, wherein the vertical leg is canted inward at an angle of about 10 degrees between the lower horizontal leg to the vertical leg.

12. The radiation scatter protection system of claim 2, wherein the plurality of additional sheets of shielding overlap each other and extend across the patient and above the X-ray table.

13. The radiation scatter protection system of claim 2, wherein the side curtain shield is removably secured to an elongated hanger strip connected to the X-ray table.

14. The radiation scatter protection system of claim 1, wherein the arm board shielding, the sand bag shield, the side curtain shield, and the throw shield are constructed of sheets of lead-impregnated rubber.

15. The radiation scatter protection system of claim 14, wherein the sheets of lead-impregnated rubber are covered on a back side and a front side with a sheet of cloth covering that are sewn together around circumference of each of the sheets.

16. The radiation scatter protection system of claim 15, wherein the sheet of cloth covering has a urethane coating on an inside surfaces against the sheet of lead-impregnated rubber for water proofing.

17. The radiation scatter protection system of claim 15, wherein the sand bag shield includes three independently moving sheets of top shielding and three independently moving sheets of bottom shielding which connect to an elongated, cylindrical sandbag.

18. A method for attaching a radiation scatter protection system to an X-ray table to limit exposure to radiation for both medical staff and patient comprising;
   disposing an arm board around an arm of the patient,
   removably mounting an arm board shielding including one large sheet of shielding and a plurality of additional sheets of shielding to the arm board,
   placing atop the patient a sand bag shield including a plurality of sheets of top shielding and a plurality of sheets of bottom shielding which connect to an elongated, cylindrical sandbag;
   hanging a side curtain shield from the X-ray table, and
   placing a throw shield atop the patient.

19. The method of claim 18, further including selecting the arm board of Polyethylene Terephthalate Glycol (PETG).

20. The method of claim 19, further including selecting the arm board shielding, the sand bag shield, the side curtain shield, and the throw shield of sheets of lead-impregnated rubber.

* * * * *